US00PP20205P3

(12) United States Plant Patent
Maloy

(10) Patent No.: US PP20,205 P3
(45) Date of Patent: Aug. 4, 2009

(54) ***VRIESEA* PLANT NAMED 'KIWI CREAM'**

(50) Latin Name: *Vriesea fosteriana*
Varietal Denomination: Kiwi Cream

(76) Inventor: Andrew Maloy, 16 Riverlea Road, Whenuapai, Waitakere (NZ), 0618

( * ) Notice: Subject to any disclaimer, the term of this patent is extended or adjusted under 35 U.S.C. 154(b) by 0 days.

(21) Appl. No.: 11/978,482

(22) Filed: Oct. 29, 2007

(65) Prior Publication Data

US 2009/0113584 P1 Apr. 30, 2009

(51) Int. Cl.
*A01H 5/00* (2006.01)

(52) U.S. Cl. ..... Plt./370

(58) Field of Classification Search ..... Plt./370
See application file for complete search history.

(56) References Cited

PUBLICATIONS

GTITM UPOVROM Citation for 'Kiwi Cream' as per NZ PBR BRO004; Oct. 5, 2005.*

* cited by examiner

*Primary Examiner*—Kent L Bell

(57) ABSTRACT

A new and distinct *Vriesea* cultivar named 'Kiwi Cream' is disclosed, characterized by very stable, strongly reticulate variegated foliage of green/yellow. Upright plant form with a cream heart.

1 Drawing Sheet

Figure 1:
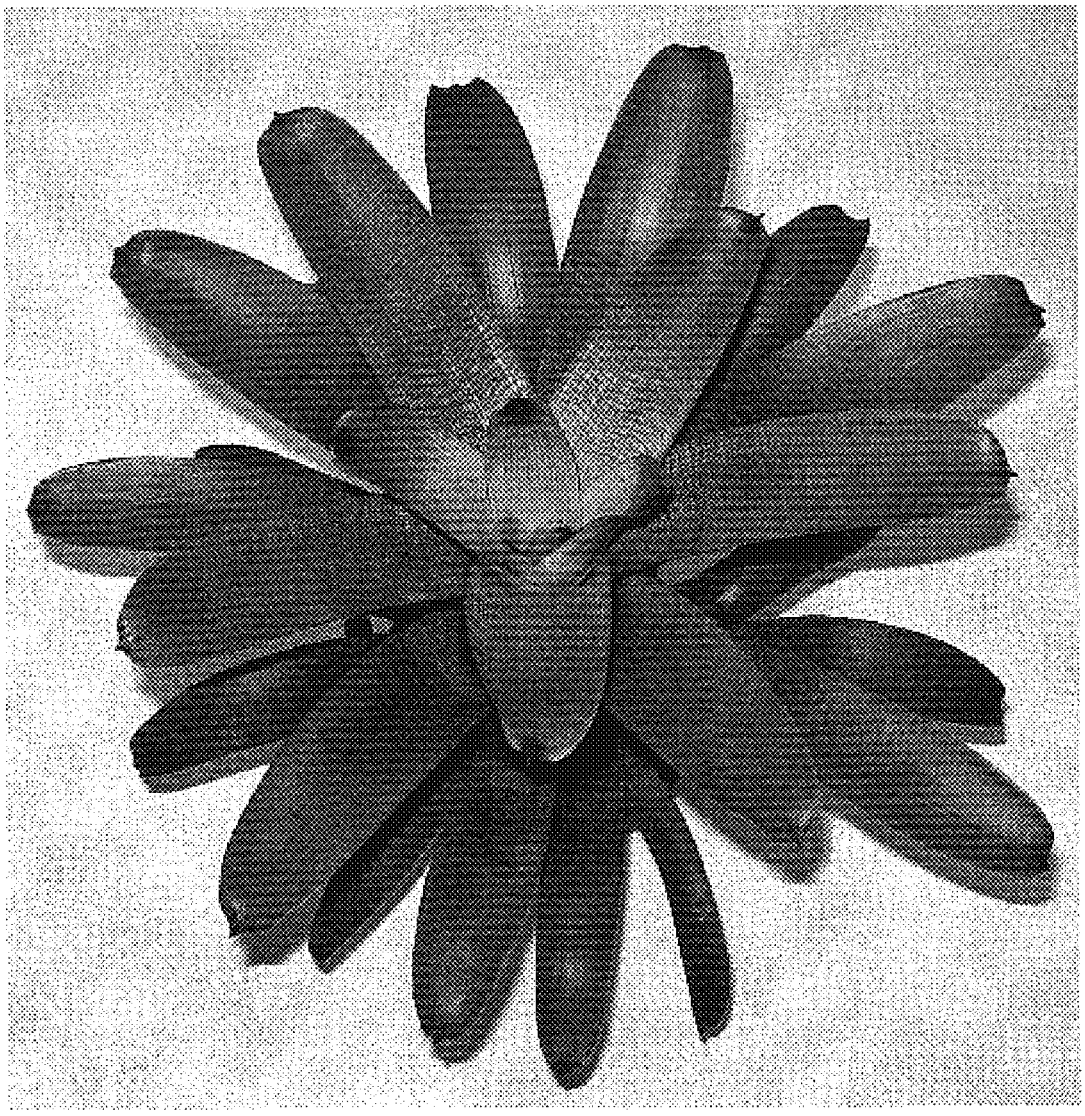

Latin name of the genus and species: *Vriesea fosteriana.* Variety denomination: 'Kiwi Cream'.

BACKGROUND OF THE INVENTION

The new cultivar is a product of a planned breeding program. The new variety originated from a cross pollination of an unnamed, seed parent and an unnamed, pollen parent, both *Vriesea fosteriana* made by the inventor during 1996.

It was discovered by the inventor, Andrew Maloy, a citizen of New Zealand, in 1999 in a group of seedlings resulting from the 1996 crossing.

Asexual reproduction of the new cultivar 'Kiwi Cream' was first performed in Auckland, New Zealand, in a commercial laboratory by tissue culture in 2002. 'Kiwi Cream' has been reproduced by micro-propagation and has shown that the unique features of this cultivar are stable and reproduced true to type.

SUMMARY OF THE INVENTION

The cultivar 'Kiwi Cream' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Kiwi Cream' These characteristics in combination distinguish 'Kiwi Cream' as a new and distinct *Vriesea* cultivar:

1. Foliage resistant to stress.
2. Foliage is green/yellow with distinct transverse markings.
3. Paler coloring at center of plant.
4. Suitability as an indoor pot plant.
5. Broad leaves occurring in right, regular whorls.

Plants of the new cultivar 'Kiwi Cream' cannot be compared to either seed parent or pollen parent as records of those characteristics were not kept. However, 'Kiwi Cream' can be compared to the commercial variety *Vriesea fosteriana* 'Red Chestnut.' Plants of 'Red Chestnut' are similar to plants of 'Kiwi Cream' in most horticultural characteristics, however, 'Red Chestnut' has a plain, uncolored heart and darker green leaves than 'Kiwi Cream.'

'Kiwi Cream' can also be compared to it seedling siblings, 'Kiwi Dusk', filed concurrently and assigned Ser. No. 11/978,481 and 'Kiwi Sunset' filed concurrently and assigned Ser. No. 11/978,480. 'Kiwi Cream' differs from 'Kiwi Dusk' in having overall much lighter foliage and a lighter center to the plant. 'Kiwi Cream' is also normally taller than 'Kiwi Dusk.' 'Kiwi Cream' differs from 'Kiwi Sunset' in having lighter foliage and a center to the plant with cream, rather than pink tones.

BRIEF DESCRIPTION OF THE PHOTOGRAPH

The accompanying photograph in FIG. 1 illustrates in full color a typical plant of 'Kiwi Cream' grown in a greenhouse. This plant is approximately 4 years, 6 months old, shown in a 17 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Kiwi Cream' plants grown in a climate controlled greenhouse in Saint Oedenrode, the Netherlands. Temperatures ranged from 18° C. to 22° C. at night to 18° C. to 22° C. during the day. No artificial light, photoperiodic treatments or chemical treatments were given to the plants. Measurements and numerical values represent averages of typical plant types.

Botanical classification: *Vriesea fosteriana* cultivar 'Kiwi Cream.'

PROPAGATION

Time to rooting: 2 months from a 2 year old tissue culture at approximately 20 to 22° C.
Root description: Fine, fibrous. Free Branching.

PLANT

Growth habit: Upright, forming compact rosettes around a single axis.
Plant shape: Inverted triangle.
Height: Approximately 44.2 cm.
Plant spread: Approximately 40 cm in a 17 cm pot.
Normal pot size: 15 cm and larger.
Growth rate: Slow.
Branching characteristics: Upright, non-branching.
Number of leaves per stem: Approximately 30.
Age of plant described: Approximately 4 years, 6 months.

FOLIAGE

Leaf:
*Arrangement.*—Whorled.
*Average length.*—Approximately 29.6 cm.
*Average width.*—Approximately 6.6 cm.
*Shape of blade.*—Oblong.
*Aspect.*—Slightly recurved.
*Apex.*—Sharply acute.
*Base.*—Decurrent.
*Margin.*—Entire.
*Texture of top surface.*—Smooth, moderately glossy.
*Texture of bottom surface.*—Smooth, moderately glossy.
*Color.*—Young foliage upper side: Near R.H.S. Yellow-green; 145A to 145D at the base, darker towards the tip; Upper half of the leaf blade is 144A with yellow-green 146A, 146B and 146C reticulate variegation. Margin at the tip is near greyed-purple; 187A. Young foliage under side: Near R.H.S. Yellow-green 145C and Yellow-green 145D, individually present. Heavily flushed greyed-red towards the tip; 178B. Outer tip greyed-purple; N186C, but slightly lighter Upper half of the leaf blade with a highly mixed, muddy reticulate variegation consisting of the individually present colors; 147A 35C and 199A. Mature foliage upper side: Near R.H.S. Green 137A and 137B, individually present. Base greyed-green; 192A and 192B present individually. Outer base greyed-orange; 166A. Upper leaf blade with a green to yellow-green reticulate variegation; Darker than 139A and 147A individually. Tip greyed-purple; 187A. Mature foliage under side: Near R.H.S. Greyed-orange; 176B to 177A and 177B, present individually, yellow-green towards the tip; 147B and 147C, present individually. Outer tip greyed-purple; N186C, but slightly lighter, whole surface colour softened by an overall greyish hue. Leaf blade with an unclear (due to the greyish layer) greyed-purple reticulate variegation; N186B, Tip; 178B.
*Venation.*—Type: Parallel. Venation coloration. Identical/Indistinguishable from foliage.
Petiole: Not present, sessile.

FLOWER

Flowering has not been observed, and is not commercially important in this cultivar.

OTHER CHARACTERISTICS

Disease and pest resistance: Neither resistance nor susceptibility to diseases or usual pests of *Vriesea,* such as scale and mealy bug, has been observed in this variety.
Drought tolerance and cold tolerance: Observed to tolerate temperatures to 35° C. without any negative effects. Temperature tolerance above this range has not been observed. Tolerance of cold temperatures have not been observed.
Fruit/seed production: Not observed.

What is claimed is:

1. A new and distinct cultivar of *Vriesea* plant named 'Kiwi Cream' as herein illustrated and described.

* * * * *